US00PP11072P

United States Patent [19]

Plate

[11] Patent Number: Plant 11,072

[45] Date of Patent: Sep. 28, 1999

[54] SINNINGIA PLANT NAMED 'GLO BLUE'

[75] Inventor: Renate Plate, Bremen, Germany

[73] Assignee: Wolfgang Bock Pflanzenexport KG, Bremen, Germany

[21] Appl. No.: 08/933,401

[22] Filed: Sep. 19, 1997

[51] Int. Cl.[6] ..... A01H 5/00

[52] U.S. Cl. ..... Plt./263

[58] Field of Search ..... Plt./68.1, 263

*Primary Examiner*—Howard J. Locker
*Assistant Examiner*—Kent L. Bell
*Attorney, Agent, or Firm*—Foley & Lardner

[57] ABSTRACT

A new and distinct variety of *Sinningia×hybrida* plant named 'Glo Blue' particularly characterized by its large dark violet, velvet textured double flowers clustered in the center of the plant. The plants grow very quickly, becoming marketable in approximately 12 weeks, and are very floriferous, often having 4–6 or more flowers open at a given time.

1 Drawing Sheet

The present invention comprises a new and distinct cultivar of *Sinningia×hybrida*, a genus in the family Gesneriaceae, and referred to by the cultivar name 'Glo Blue'. The new cultivar is a hybrid selected from the progeny of a cross of parent plants identified below.

Hybrids of *Sinningia speciosa*, or Gloxinia as they are commonly known, are popular potted plants which may be cultivated indoors or in greenhouses. They are distinguished by their large, showy velvet textured flowers which come in various shades of violet, rose, red, or white.

Sinningia are typically propagated from seeds, or by leaf cuttings or tissue culture. The new cultivar is a sterile hybrid which does not produce any seeds and is propagated from tissue culture as clones.

The new cultivar is a product of a breeding program carried out by the inventor Renate Plate in Bremen, Germany. The new cultivar named 'Glo Blue' is a result of several generations of crosses of selected, but unnamed *Sinningia speciosa* made by the inventor beginning in 1994. The new cultivar 'Glo Blue' was discovered by the inventor from the progeny of the stated cross in 1995. Asexual propagation by tissue culture done under the supervision of the inventor in Bremen, Germany was used to increase the number of plants for evaluation and has demonstrated the stability of the combination of characteristics from generation to generation.

The following observations, measurements and values describe plants grown in Apopka, Fla. in greenhouse conditions which are typical of those generally used in horticultural practice.

The following traits have been repeatedly observed to be characteristics which in combination distinguish 'Glo Blue' from generally available seedling-derived Sinningia common in commercial cultivation.

1. The flowers produced by 'Glo Blue' are double, large, dark violet in color, and are clustered in the center of the plant.

2. Plants of 'Glo Blue' have a short, compact growth habit, and are suitable for cultivation in 10–15 cm pots.

3. Plants of 'Glo Blue' are very floriferous, typically having 4–6 flowers, and 10 or more buds in various stages of development and which open in succession. Once in bloom, the plant typically remains in bloom for 12 weeks.

4. Plants of 'Glo Blue' grow very quickly, producing marketable flowering plants in approximately 12 weeks.

It is difficult to compare the new cultivar with seed-derived Sinningia which are heterogeneous genetically, and therefore lack uniformity in flower color and quality. By comparison, 'Glo Blue' is a single superior genotype asexually propagated preferably by tissue culture. Thus, its combined horticultural properties listed above are uniform and predictable.

All color references are measured against The Royal Horticultural Society Colour Chart. Colors are approximate as color depends on horticultural practices such as light level and fertilization rate, among others, without, however, any change in genotype.

The color photographic drawing comprises a top perspective view of the flowers and foliage of a plant of 'Glo Blue' grown in a 15 cm pot. The photograph was taken approximately 16 weeks after planting a small cutting obtained by tissue culture and grown under appropriate growing conditions.

Colors are as accurate as possible with color illustrations of this type.

Origin: Seedling from a cross of selected, but unnamed *Sinningia speciosa.*

Classification: *Sinningia×hybrida*, cv 'Glo Blue'.

Propagation: Asexual propagation by tissue culture or leaf cuttings.

Flowers:

*Calyx.*—6–8 lobed, lobes lanceolate, acutely tapered. Approximately 2.5 cm to 2.8 cm long, and 1.2 cm to 1.5 cm wide. Adaxial color is greener than, but closest to 137 A; abaxial color is 137 B.

*Corolla.*—Campanulate, outermost whorl has approximately 6 lobes. Secondary inner whorls of corolla are somewhat ruffled in appearance. The number of lobes is variable, 7 to 9. Corolla is approximately 4.9 cm to 5.5 cm long, and 7.8 cm to 8.7 cm in diameter. Adaxial color when lobes are fully open is considerably darker than, but closest to 83 A, becoming lighter (83 B) near the margins of the lobes. The tube of the corolla is 187 A. The base of the tube is 59 B speckled with 187 A. The abaxial color of the lobes is 83 C–D, with areas of 85 D near the base and occasional streaks of green 146 D, 145 D. The corolla darkens to 187 A with senescence.

*Peduncle.*—Approximately 8.0 cm to 8.7 cm long, and 6 mm to 7 mm in diameter measured at the midpoint between the calyx and the stem. Color is 146 C.

*Bud.*—Tightly folded, enclosed in the calyx, round, 0.8–1.5 cm in width, light green in color, R.H.S. 147 C–D, but it rapidly expands and partially opens/unfolds to take on the colors of the mature flower.

*Flowering habit.*—Flowers borne singularly, carried above the foliage, one flower per stem; there frequently are two flower stems per leaf node.

*Arrangement of flowers.*—The flowers are clustered together above the foliage in the center of the plant.

*Texture of flowers.*—Thick and velvety in appearance.

*Quantity of bloom.*—Plants of 'Glo Blue' are very floriferous, typically having 4–6 flowers, and 10 or more buds in various stages of development and which open in succession.

*Duration of bloom.*—Once in bloom, the plant typically remains in bloom for approximately 12 weeks. Individual flowers remain open for approximately 14 days before senescence.

*Fragrance.*—None.

*Reproductive organs.*—Stamens, anthers are reduced in size and misshapen, frequently petaloid, coherent with the corolla. Style and stigma are reduced in size, and frequently petaloid, 155 A in color. Ovary is reduced in size.

*Seed characteristics.*—Sterile hybrid.

Plant:

*Form.*—Basal rosettes of rugose velvet texture, elliptic, paired, opposite leaves arranged around short stems.

*Height.*—Approximately 14.5 cm to 16.0 cm, including flowers.

*Diameter.*—Approximately 27 cm to 31 cm.

*Stems.*—Approximately 0.5 cm to 0.7 cm in diameter. Internodes approximately 0.4 cm to 1.0 cm. Stem color is 146 C–D.

*Resistance to pests and disease.*—Typical, no special obsurvations made.

Foliage:

*Size of leaf.*—The largest leaves are approximately 12.9 cm to 13.2 cm long, and 10 cm to 10.5 cm wide. Average sized leaves are approximately 10.5 to 11 cm long, and 8.5 cm to 9.2 cm wide.

*Shape of leaf.*—The leaf blade is ovate with an obtuse to cordate base and an obtuse to acute tip. The leaf petioles are approximately 3.8 cm to 5.3 cm long and 0.4 cm to 0.6 cm in diameter measured at the midpoint between the stem and the leaf. The leaf margins are crenate, and somewhat wavy. The leaf blade may be characteristically flat or cupped.

*Surface texture.*—The upper surfaces of the leaf are rugose and pubescent. The veins and midrib are sunken on the upper surface, and protruding on the lower surface. The color of the veins and midrib is 146 D on the adaxial surface and 148 C–D on the abaxial surface.

*Color.*—The leaves are dark green throughout. The adaxial surface is 137 A, and the abaxial surface is 148 C–D. The petioles are 146 D.

Roots: Stems arise from a fleshy tuber which is approximately 3.8 cm to 4.7 cm in diameter at the time of flowering. The tuber is brownish white, and has numerous greenish white to brown fibrous roots.

I claim:

1. A new and distinct cultivar of *Sinningia×hybrida* plant named 'Glo Blue', as illustrated and described.

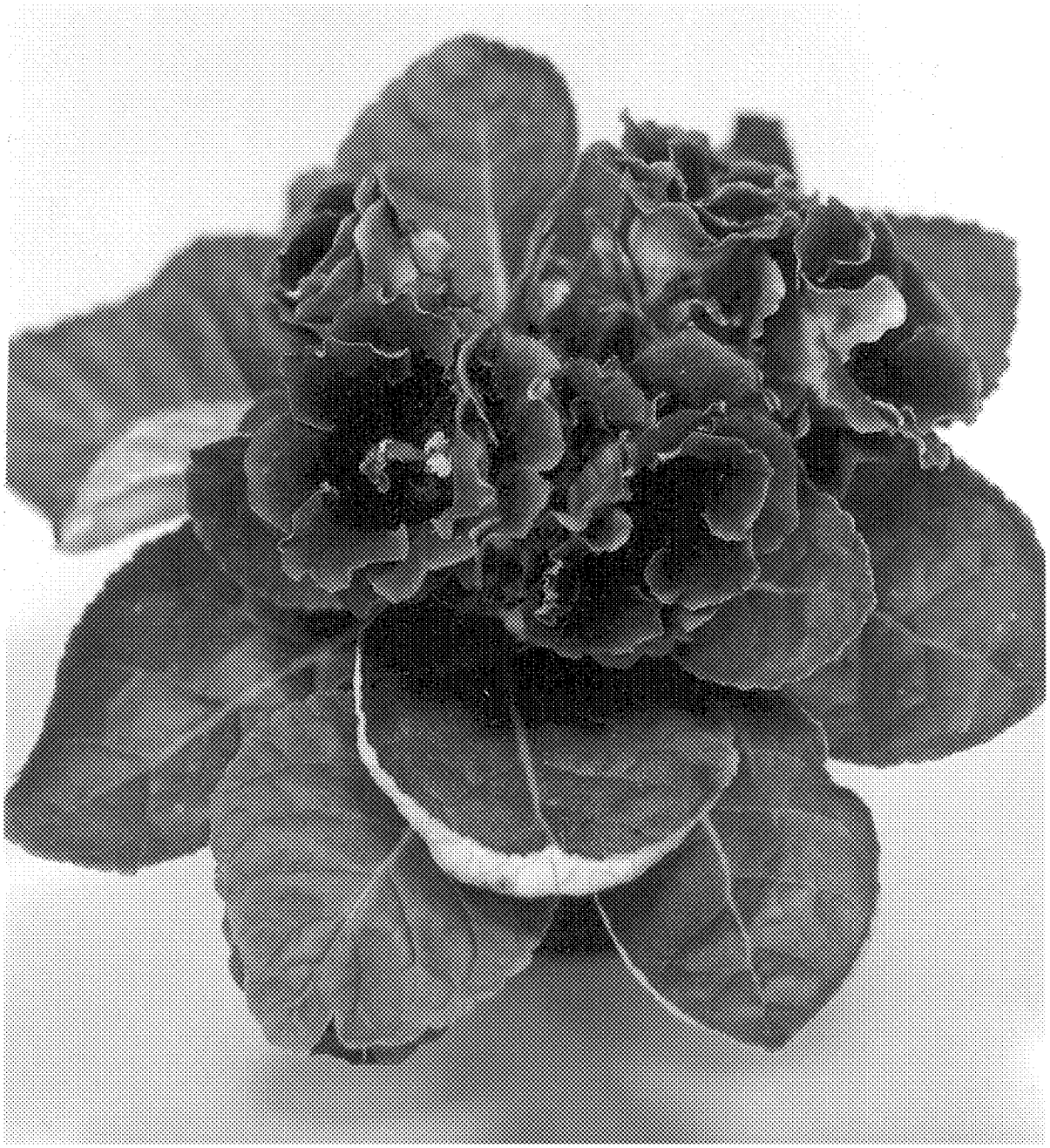

* * * * *